United States Patent
Suskind et al.

(10) Patent No.: US 7,226,605 B2
(45) Date of Patent: Jun. 5, 2007

(54) BOTULINUM TOXIN IN THE TREATMENT OR PREVENTION OF ACNE

(75) Inventors: Dana L. Suskind, Chicago, IL (US);
Ann H. Tilton, Metairie, LA (US);
Mary L. Caire, Dallas, TX (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 88 days.

(21) Appl. No.: 10/483,154

(22) PCT Filed: Jul. 25, 2002

(86) PCT No.: PCT/US02/23670

§ 371 (c)(1),
(2), (4) Date: Jan. 8, 2004

(87) PCT Pub. No.: WO03/011333

PCT Pub. Date: Feb. 13, 2003

(65) Prior Publication Data

US 2005/0074466 A1    Apr. 7, 2005

Related U.S. Application Data

(60) Provisional application No. 60/308,205, filed on Jul. 27, 2001.

(51) Int. Cl.
*A61K 39/08* (2006.01)
(52) U.S. Cl. .................................................. 424/247.1
(58) Field of Classification Search ............ 424/247.1, 424/239.1, 236.1, 94.2, 94.63; 514/44, 14
See application file for complete search history.

(56) References Cited

U.S. PATENT DOCUMENTS

| | | | | | |
|---|---|---|---|---|---|
| 4,524,065 | A | * | 6/1985 | Pinnell | 424/94.2 |
| 4,885,282 | A | * | 12/1989 | Thornfeldt | 514/53 |
| 5,562,907 | A | * | 10/1996 | Arnon | 424/236.1 |
| 5,670,484 | A | * | 9/1997 | Binder | 514/14 |
| 5,766,605 | A | * | 6/1998 | Sanders et al. | 424/239.1 |
| 6,146,626 | A | * | 11/2000 | Markert et al. | 424/94.63 |
| 6,447,787 | B1 | * | 9/2002 | Gassner et al. | 424/247.1 |
| 6,896,886 | B2 | * | 5/2005 | Aoki et al. | 424/184.1 |
| 2002/0086036 | A1 | * | 7/2002 | Walker | 424/236.1 |
| 2002/0102275 | A1 | * | 8/2002 | Graham | 424/247.1 |
| 2002/0107199 | A1 | * | 8/2002 | Walker | 514/12 |
| 2003/0021775 | A1 | * | 1/2003 | Freeman | 424/94.63 |
| 2003/0113349 | A1 | * | 6/2003 | Coleman, III | 424/239.1 |
| 2005/0220820 | A1 | * | 10/2005 | Sanders et al. | 424/239.1 |

OTHER PUBLICATIONS

Mengesha, YM et al, Am. J. Clin. Dermotol., 2002, vol. 3(6), pp. 389-400, Pustular skin disorders, diagnosis and treatment.*
Cohn, MS e tal, Cutis, Oct. 1993, vol. 52(4), pp. 205-208, abstract only.*
Heckmann, Marc et al, The New England Journal of Medicine, vol. 344(7), Feb. 15, 2001, pp. 488-493.*
Kinkelin, I e tal, Effective Treatment of frontal hyperhidrosis with botulinum toxin A, British Journal of Dermatology, vol. 143, pp. 824-827, 2000.*
Gill, D. Michael, Microbiological Review, Mar. 1982, pp. 86-94, vol. 46(1), Bacterial toxins, A table of lethal amounts.*
Brin, M.F., "Botulinum toxin: Chemistry, Pharmacology, Toxicity, and Immunology," *Muscle and Nerve* Supp. 6, pp. S146-S168 (1997).
Fitzpatrick, T. et al., Color Atlas & Synopsis of Clinical Dermatology: Common and Serious Diseases (4th Ed. 2001), pp. 2, 18, 30, 45, 50-51.
Johnson, B. et al., "Use of Systemic Agents in the Treatment of Acne Vulgaris," *American Family Physician*, vol. 62, pp. 1823-1830, 1835-1836 (2000).
Kinkelin, I. et al., "Effective Treatment of Frontal Hyperhidrosis with botulinum toxin A," *Brit. J. Dermatol.*, vol. 143, pp. 824-827 (2000).
Krowchuk, D.P., "Managing Acne in Adolescents," *Pediatric Dematology*, vol. 47, No. 4, pp. 841-857 (Aug. 2000).
Roenigk, H.H., Jr., "Combination Resurfacing," *Dermatologic Therapy*, vol. 13, pp. 215-222 (2000).

* cited by examiner

*Primary Examiner*—Mark Navarro
*Assistant Examiner*—Ginny Allen Portner
(74) *Attorney, Agent, or Firm*—John H. Runnels; Bonnie J. Davis

(57) ABSTRACT

*Botulinum* toxin may be used to inhibit the cascade of events leading to acne. Results in preliminary studies have been dramatic. Without wishing to be bound by this theory, it is believed that *botulinum* toxin achieves this result through parasympathetic effects, inhibiting sweat gland activity, stimulating keratinocyte locomotion, anti-inflammatory effects, and possibly anti-androgenic effects. *Botulinum* toxin can play an important role in decreasing and even preventing the formation of acne.

29 Claims, No Drawings

BOTULINUM TOXIN IN THE TREATMENT OR PREVENTION OF ACNE

The benefit of the 27 Jul. 2001 filing date of U.S. provisional patent application Ser. No. 60/308,205 is claimed under 35 U.S.C. § 119(e) in the United States, and is claimed under applicable treaties and conventions in all countries.

TECHNICAL FIELD

This invention pertains to a method for the treatment or prevention of acne vulgaris, particularly to the use of *botulinum* toxin to treat or prevent acne.

BACKGROUND ART

Acne vulgaris

While not life-threatening, acne vulgaris can cause significant problems for affected individuals. Depending on its severity and other factors, recalcitrant acne can be psychologically debilitating, and can impose significant financial and emotional costs on those whom it afflicts. Despite some recent successes in acne therapy, treatment failures are still common, especially in adult women. While many adults "outgrow" this disease, there are some who continue to be afflicted during much of adulthood, despite continued medical advances. Unfortunately, the most potent acne medication in current use is administered systemically via a treatment that is teratogenic, an important issue for many women. There is an unfilled need for a more localized and effective treatment for acne, one with minimal side effects.

Acne, which most commonly occurs during adolescence, is influenced by several factors. The pathology centers on the pilosebaceous follicle, comprising the sebaceous gland, the follicle (pore), and the vellus hair. Factors that promote the formation of comedones (whiteheads or blackheads) include the following: (1) increased sebum production, (2) inflammation of the dermis and follicles by inflammatory mediators, (3) hyperkeratinization and obstruction of the upper region of the follicle, and (4) colonization of the follicle by the bacterium *Propionibacterium* acnes, Adolescence is marked by an increase in levels of circulating androgens, particularly dehydroepiandrosterone sulfate (DHEAS). The increased androgen levels are thought to cause sebaceous glands to enlarge and to increase sebum production. While most acne patients have normal hormone levels, there are reasons to conclude that increased sebum production plays an important role in acne. For example, there is a correlation between the rate of sebum production and the severity of acne. In addition, acne patients typically produce sebum that is deficient in linoleic acid, which is a potential cause of abnormal keratinization and follicular obstruction.

In response to increased sebum levels, *Propionibacterium* acnes, a gram positive, anaerobic, diphtheroid bacterium, often colonizes the sebaceous follicles. P. acnes exacerbates acne by acting as a chemo-attractant for neutrophils (a type of white blood cells, also called polymorphonuclear leukocytes, or PMNs). The neutrophils ingest the P. acnes, and in doing so release various hydrolytic enzymes that damage the follicular wall. The released follicular contents then invade the dermis and cause an inflammatory reaction, manifesting as pustules, erythematous papules, or nodules. In a separate route, P. acnes can hydrolyze triglycerides to free fatty acids, which also increase inflammation and follicular obstruction. P. acnes may also activate the complement components of the immune system, which can also lead to follicular obstruction.

The follicles are lined with squamous epithelium, a layer of cells that is contiguous with the skin surface. In an acne-prone individual, the shedding of cells from this lining is often impeded, perhaps due to an increased level of intracellular adhesion that promotes the retention of cells. The retained cells can obstruct the follicles, resulting in comedones. The exact cause of this inhibited shedding is unknown, but it may be related either to abnormalities in epidermal differentiation, or to abnormal sebum composition (e.g., a deficiency in linoleic acid).

It has also been demonstrated that increased sebum levels can irritate keratinocytes, causing the release of interleukin-1, which in turn can cause follicular hyperkeratinization.

The final common pathway in each of these acne-causing routes, which are not mutually exclusive, is follicular obstruction.

Current Acne Therapies

Currently-used acne therapies are directed at various aspects of the acne cascade. The most commonly used therapy is probably topical benzoyl peroxide, which has an antibacterial effect, and which may also decrease free fatty acids, resulting in a decrease in inflammation and follicular obstruction.

Topical and systemic antibiotics have been used to target P. acnes. The antibiotics that have been used for this purpose include erythromycin, tetracycline, clindamycin, and doxycycline. Predictably, the prolonged use of antibiotics often leads to the development of resistant strains of P. acnes.

Topical and systemic retinoids (derivatives of vitamin A) have been used to normalize the keratinization of the follicle, decreasing follicular obstruction and rupture. Systemic isotretinoin (Accutane™), which is highly effective for acne, unfortunately has serious adverse effects, most notably teratogenicity. Topical retinoids include tretinoin (Retin-A™), whose chemical structure is similar to that of isotretinoin.

The current state of the art in treating acne is summarized, for example, in the following two review articles: D. Krowchuk, "Managing Acne in Adolescents," *Pediatric Dermatology*, vol. 47, pp. 841-857 (2000); and B. Johnson et al., "Use of Systemic Agents in the Treatment of Acne Vulgaris," *American Family Physician*, vol. 62, pp. 1823-1830, 1835-1836 (2000).

Advances in acne therapy have followed better understanding of its multiple causes. Most treatments are directed at normalizing keratin production (e.g., through the use of retinoids), or at controlling bacterial colonization. To the inventors' knowledge, no prior treatments have sought to affect either sweat gland production or keratinocyte locomotion, both of which can be factors in the follicular occlusion that leads to acne.

*Botulinum* Toxins and Pharmacology

*Clostridium botulinum*, an anaerobic bacterium, produces seven toxins that have similar neurotoxic effects, but that are antigenically distinct: serotypes A through G. These toxins are potent neuroparalytic agents that inhibit the release of acetylcholine at neuromuscular junctions and at neuroglandular junctions. See M. F. Brin, "*Botulinum* toxin: Chemistry, Pharmacology, Toxicity, and Immunology," *Muscle and Nerve Supp.* 6, pp. S146-S168 (1997); and 1. Kinkelin et al., "Effective Treatment of Frontal Hyperhidrosis with *botulinum* toxin A," *Brit. J. Dermatol.*, vol. 143, pp. 824-827 (2000).

Neither the synthesis nor the storage of acetylcholine is affected by *botulinum* toxin. Therefore, its effects are temporary. *Botulinum* toxin penetrates the endosomal membrane into the cytosol, where the secretion of acetylcholine is blocked. *Botulinum* toxin also appears to possess anti-inflammatory effects. Studies of the effect of *botulinum* toxin on glandular function have observed that its effects occur at the presynaptic terminal of the parasympathetic cholinergic nerves.

*Botulinum* toxin A (sold under the trademark Botox® by Allergan (Irvine, Calif.), and under the trademark Dysport® by Ipsen Limited (Maidenhead, Berkshire, United Kingdom)) has been used for certain therapeutic purposes at both neuroglandular and neuromuscular junctions. Its temporary neuromuscular blockade has found numerous previous uses, including the treatment of strabismus, migraines, achalasia, hemifacial spasm, rhytids, and spastic dysphonia. The injections have proven to be safe and effective for these purposes, with only minor side effects such as local swelling and transient weakness of nearby muscles. *Botulinum* toxins A and B have been reported to be well tolerated in patients who have used it.

Intracutaneous *botulinum* toxin A has become a primary therapy for axillary, palmar, solar, and frontal hyperhidrosis (excessive sweating), as well as for gustatory sweating (Frey's Syndrome). It has also been shown to be an effective alternative to surgery in Hailey-Hailey disease, a benign familial pemphigus that affects primarily the groin and axillary folds (areas of high moisture).

Studies have found no long-term effects of *botulinum* toxin A in human tissue. Histological studies have found no nerve fiber degeneration, and no sweat gland atrophy as a result of therapy. Antibodies to *botulinum* toxin A have been found in fewer than 5% of patients receiving *botulinum* toxin A injections. There have been no reported cases of anaphylaxis in response to injections of *botulinum* toxin A.

*Botulinum* toxin B (sold under the trademark Myobloc™ and NeuroBloc™ by Elan Pharmaceuticals (Dublin, Ireland)) has been approved by FDA for use in treating patients with cervical dystonia.

All seven *botulinum* toxin serotypes (A through G) are available commercially from Metabiologics, Inc. (Madison, Wis.).

Neuromuscular Junction Blockade

The first reported clinical use of *botulinum* toxin A was its use in the treatment of strabismus in the 1970's. Injecting the small extraocular muscles resulted in a realignment of the muscles, straightening of the globe, and improvement of visual alignment in some cases. Subsequently, *botulinum* toxin A has been used therapeutically for several other purposes, both functional and cosmetic. It has proven effective in treating focal dystonias, spasmodic dysphonia, blepharospasm, hemifacial spasm, torticollis, and cervical dystonia. It has also recently been used in facial plastic surgery, especially to treat rhytids (wrinkles).

In 1990, the use of *botulinum* toxin A was reported in ambulatory and nonambulatory cerebral palsy patients, namely by injecting different muscle groups to treat spastic diplegia. For example, double-blinded, placebo-controlled studies on the effect of *botulinum* toxin A on limb dystonias and spasticity have found significant subjective as well as objective benefits.

The American Academy of Ophthalmology, the American Academy of Neurology, the American Academy of Otolaryngology, and the National Institutes of Health have all released statements supporting the therapeutic efficacy of *botulinum* toxin A for a variety of clinical conditions. Among the conditions for which *botulinum* toxin A has been used are blepharospasm, strabismus, cervical dystonia, spasmodic torticollis, rhytids, hemifacial spasm, facial spasm, spasmodic dysphonia, focal hand dystonia, hyperfunctional facial wrinkles, Frey's syndrome, hyperhidrosis, adult spasticity, adjunctive treatment of spasticity in cerebral palsy, oromandibular dystonia, and other dystonias.

Neuroglandular Junction Blockade

The effects of *botulinum* toxin A as an anticholinergic agent at the neuroglandular junction have not been explored as extensively as those occurring at the neuromuscular junction. Clinical studies examining the effect of intracutaneous *botulinum* toxin for focal hyperhidrosis found complete abolition of sweating in the injected area within 3 to 7 days. No adverse effects were reported, and in a five month follow-up there were no clinical recurrences of the hyperhidrosis. See generally I. Kinkelin et al., "Effective Treatment of Frontal Hyperhidrosis with *botulinum* toxin A," *Brit. J. Dermatol.*, vol. 143, pp. 824-827 (2000).

Gustatory sweating is another area of neuroglandular dysfunction in which *botulinum* toxin A has proven effective. Gustatory sweating (or Frey's syndrome) is a disabling disorder in which the cheek skin sweats profusely during eating. The syndrome often occurs after parotidectomy, and may be due to the misdirection of the regenerating parasympathetic fibers that enervate the sweat glands of the face. Intracutaneous *botulinum* toxin A has been reported to significantly decrease or prevent sweating for over six months, with no clinical evidence of facial weakness in any patients.

*Botulinum* toxin A injected into the submandibular glands has been reported to significantly decrease salivation resulting from stimulation of the lingual nerves. The decreased salivation was temporary, and did not appear to be directly toxic to the acinar cells of the gland. See D. Suskind et al., "Clinical study of *botulinum* A toxin in the treatment of sialorrhea in children with cerebral palsy," *Laryngoscope*, vol. 112, pp. 73-81 (2002).

Canine studies have also shown that vasomotor rhinorhea, a parasympathetically controlled phenomenon, responds to topical *botulinum* toxin A.

While the duration of *botulinum* toxin A's action at the neuromuscular junction appears to be about three months, there appears to be a longer-lasting effect at the glandular level. *Botulinum* toxin A has produced anhydrosis for over 12 months in patients with gustatory sweating. The reason for the difference in duration of action is uncertain. Hypotheses include a higher rate of re-synthesis of SNAP-25 (the protein cleaved by *botulinum* toxin) in neuromuscular synapses, and a higher area of axonal sprouting and consecutive reinervation of muscle fibers as compared to that in glandular tissue.

To the inventors' knowledge, there have been no prior suggestions that *botulinum* toxin might be used in the treatment or prevention of acne.

DISCLOSURE OF THE INVENTION

We have discovered that *botulinum* toxin may be used to inhibit the cascade of events leading to acne. Results in preliminary studies with *botulinum* toxin A have been dramatic. Without wishing to be bound by this theory, it is believed that *botulinum* toxin achieves this result through parasympathetic effects, inhibiting sweat gland activity, and stimulating keratinocyte locomotion. Associated anti-inflammatory and anti-androgenic effects may also contribute. Treatments may be repeated periodically as needed to inhibit the recurrence of acne, typically at intervals between about 3 months and about 6 months, preferably about once every 4 months.

Without wishing to be bound by this theory, we believe that *botulinum* toxin inhibits the formation of acne through at least three different pathways. First, *botulinum* toxin inhibits sweat production by sweat glands. Decreased perspiration may clinically improve acne by decreasing the growth of *P. acnes*. Thus the ability of *botulinum* toxin to decrease perspiration leads to decreased acne. Second, follicular occlusion by keratinocytes is the final common pathway in each of the various routes leading to acne. Keratinocyte locomotion is inhibited by the high dose stimulation of nicotinic acetylcholine receptors. By inhibiting the release of acetylcholine, *botulinum* toxin may indirectly increase the migration of keratinocytes, thus reducing follicular occlusion. Third, the androgen surge during puberty is a known instigator of acne, and studies have shown that androgens increase the number of acetylcholine receptors. Interestingly, androgen receptors are found on pilosebaceous duct keratinocytes, which are important in follicular occlusion. Thus we believe that during puberty androgens increase the number of acetylcholine receptors on the pilosebaceous keratinocytes, leading to further inhibition of keratinocyte locomotion through increased acetylcholine stimulation. By inhibiting the release of acetylcholine, *botulinum* toxin decreases the number of acetylcholine receptors on the pilosebaceous keratinocytes, thereby increasing keratinocyte locomotion through decreased acetylcholine stimulation. Additionally, *botulinum* toxin may have anti-inflammatory effects.

MODES FOR CARRYING OUT THE INVENTION

EXAMPLE 1

The "index case" was a Caucasian woman in her late twenties who had been afflicted by severe cystic acne since puberty. She experienced a complete resolution of her acne following intracutaneous *botulinum* toxin A injections. An otherwise healthy woman, she had tried several prior medical treatments for her acne, including both spironolactone and three courses of isotretinoin, without resolution.

Following initial injections of *botulinum* toxin A, her forehead, which had previously been covered with deep cystic lesions, completely resolved.

She now receives *botulinum* toxin A injections in her forehead, chin, and cheek/nasolabial fold area approximately once every six months. After about six months, the cysts begin to recur. They resolve about one week after injections. Injections are spaced approximately 1.5 cm apart from one another, and the dose per injection site is about 2.5 U.

Her physical examination now demonstrates an attractive blonde woman with strikingly clear skin. Her facial nerve is intact, with only slight to moderate weakness of her frontalis muscles. She states that the *botulinum* toxin A injections and the resulting resolution of her acne have had a profound effect upon her life, both socially and psychologically.

A dermatologist has confirmed the substantial improvement in this patient's condition.

EXAMPLE 2

A Caucasian woman in her early thirties presented with severe cystic acne, which she had since puberty, and which had not responded to traditional treatments. She already had severe scarring as a result of her acne. Injections of *botulinum* toxin A were made in her back. Within one week there was a substantial decrease in acne in the injected region, and by one month there a significant decrease in the papules and pustules. A discernable demarcation line was visible where the injections ended, as there were active lesions around the periphery, beginning about 1 cm from the zone where the injections had been made. A total of 86 units of *Botulinum* toxin A were used, 2.5 units per injection at injection sites spaced about 2-3 cm from one another.

A dermatologist has confirmed the substantial improvement in this patient's condition. The improvement lasted for about five months prior to the return of pruritus and papules.

EXAMPLE 3

A 20-year-old Caucasian man who had severe cystic acne since puberty presented with acne involving his face, neck, chest, and back. He had previously undergone two courses of isotretinoin, as well as many courses of systemic and topical antibiotic treatments, all without resolution of his acne. His only other significant medical problem was Crohn's colitis. A total of 162 U of *botulinum* toxin A was injected into his back, but not the other areas where acne was present. There was a substantial clearing of the treated areas after one week, and almost complete clearing after three weeks. By contrast, there was no improvement in the untreated areas (i.e., face, neck, and chest).

A dermatologist has confirmed the substantial improvement in this patient's condition. The clearing persisted for five months during follow-up observations.

Although the number of patients in whom the *botulinum* toxin treatment has been tested in this initial experiments was small—only three patients—dramatic improvements were seen in 100% of these initial patients, all of whom had recalcitrant cases of acne that had not responded to conventional treatments. A subsequent, small-scale clinical study has now been conducted as well, with the results reported below.

EXAMPLE 4

A small-scale clinical study is being conducted to examine the clinical benefit of intradermal *botulinum* toxin A (Botox™) injections in the prevention or reduction of acne vulgaris lesions in adults. As of the filing date of this application, this study is ongoing, but some preliminary results were available. The protocol being used in this study is as follows:

The study is an open-label, prospective, single-center, pilot study. Fifteen subjects are to begin participation in the study. Informed consent is obtained from all subjects.

Eligibility Criteria

Eligibility Criteria are as Follows:

Inclusion

1. Males or females.
2. General good health as determined by the initial paperwork.
3. Willingness to have clinical examinations and photographs of the face and back.
4. Diagnosis of recalcitrant acne (unresponsive to conventional therapy, including systemic antibiotics).

5. Negative pregnancy test (females).
6. At least 10 of the 15 subjects enrolled into the study will have cystic acne on the forehead or back (at least half must be forehead).
7. Up to 5 subjects will have non-cystic inflammatory acne on the forehead or back (at least 3 must be forehead).
8. Individuals must be willing to serve as a no-treatment control group. Three of the 15 subjects were assigned to the no treatment group (at least 2 from the cystic group and 1 from the non-cystic group).
9. Able to understand the requirements of the study and sign an informed consent form.
10. Willingness to remove facial makeup no less than 30 minutes prior to each facial exam.

Exclusion

1. Females who had begun treatment with estrogens or birth control pills for 12 weeks or less prior to baseline.
2. Subjects with any skin disease that might interfere with the diagnosis or evaluation of acne.
3. Subjects currently participating in an investigational drug study or who had participated in one within 30 days of the baseline visit.
4. Individuals with uncontrolled metabolic disease such as diabetes, hypertension, hyperthyroidism, or hypothyroidism as determined by the health questionnaire.
5. Women known to be pregnant, nursing, or planning to become pregnant within the next six (6) months as determined by the initial paperwork.
6. Individuals having an allergy or sensitivity to *botulinum* toxin A.
7. Individuals with a history of poor cooperation, non-compliance with treatment, or unreliability in previous clinical studies.
8. Individuals with a history of Myasthenia Gravis or Eaton Lambert Disease.
9. Individuals who had a change in antibiotic use within the last 1.5 months.
10. Individuals who were receiving aminoglycocides, anti-cholinesterases, magnesium sulfate and other drugs or products that interfere with neuromuscular transmission.
11. Individuals who have had treatments with or exposure to *botulinum* toxin A.

Individuals are admitted to study at the discretion of the investigator based on medical history and findings of the pre-study interview and examination. Each subject is expected to complete the full course of the study.

Conduct of Study

Procedures

Visit 1—Screening

Prospective subjects complete a health/eligibility questionnaire, a photography release form, a confidentiality agreement, and an informed consent agreement. Those who qualify are examined on the face and back for the presence of cystic or inflammatory acne.

Fifteen qualified subjects, as described in the eligibility criteria, enroll in the study and return for baseline in 1-3 days.

Subjects are placed into a treatment group based on the location of their acne (forehead or back). Each subject is treated either on the forehead or back, but not both. Randomization of treatment groups occurs between Visits 1 and 2 (after all individuals are screened and all subjects are enrolled).

Visit 2—Baseline

Subjects return to the clinic 1-3 days after the qualification visit. Subjects who in both the treatment group and the control group completed a pre-injection questionnaire.

A trained clinical grader counts papules, pustules, open comedones, closed comedones, and cysts at the test site. The grader also assesses erythema and elevation of the lesions, as well as dryness and oiliness of the surrounding skin. A single cross-polarized photograph is taken of the test site.

A topical anesthetic cream is applied to the test sites prior to injections. The study investigator performs Botox™ injections in the forehead with a distance between adjacent injection points ranging from 1.5 to 2 cm. Control patients were injected with saline only. No injections are performed closer than 1.5 cm to the brow to prevent ptosis. The intracutaneous nature of the injections is expected to decrease the likelihood of muscle weakness (as compared to *botulinum* toxin injections for treating wrinkles. Injections on the back are conducted on a similar spacing, depending on the individual's acne distribution. Approximately 2.5-3 mouse units of Botox™ are injected into each area, as otherwise described in M. Naumann et al., "Focal Hyperhidrosis: Effective Treatment with Intracutaneous Botulism Toxin," *Arch. Dermatol.*, vol. 134, pp. 301-304 (1998); and M. Naumann et al., "Treatment of Gustatory Sweating with Botulism Toxin," *Ann. Neurol.*, vol. 42, pp. 973-975 (1997). The dilution is 3 units per 0.05 cc, equivalent to 1.66 cc per 100 units of *botulinum* toxin A. The upper dose limits are 80 units for the forehead, and 125 units for the back. Subjects remain in the clinic for 30 minutes after receiving injections. The subjects' current acne regimens are continued.

Subjects are given a calendar of future visits. A clinician reviews study instructions with each subject, and gives them a written copy for use at home.

Visits 3-7—Further Evaluations

Subjects return to the clinic approximately 1, 2, 4, 8 and 12 weeks after treatment (Visits 3, 4, 5, 6 and 7, respectively). Evaluations are performed at each visit as described for baseline, but no further injections are administered. On each visit, subjects complete a questionnaire; and a trained clinical grader performs acne lesion counts, grades lesions for erythema and elevation, and grades surrounding skin for dryness and oiliness. A single cross-polarized photograph is repeated at each test site.

Any adverse events are noted.

If a subject fails to return for a scheduled examination, a staff member attempts to contact the subject to determine whether the subject has continued to follow study instructions and intends to continue participation in the study. The subject is processed as soon as possible, or is allowed to miss a study visit at the discretion of the investigator. Subjects lost from the study are documented.

EXAMPLES 5-9

Preliminary Results

As previously mentioned, this study is ongoing as of the filing date of this application. Preliminary results from a portion of the study that has been completed are reported below.

Results after 12 weeks for the 5 subjects in the "back" group are summarized in Table 1.

TABLE 1

| "Back" Group (n = 5) | | | | | | |
|---|---|---|---|---|---|---|
| Variable | Mean Baseline Score | Mean Score after 12 weeks | Mean Change, Baseline to 12 weeks | Percent Change in Mean, Baseline to 12 weeks | Standard Error of the Mean, Baseline to 12 weeks | P (change, baseline to 12 weeks) ** = statistically significant change ($P < 0.05$) |
| Papules | 19.0 | 4.8 | −14.2 | −75% | 5.3 | 0.01** |
| Pustules | 1.8 | 0 | −1.8 | −100% | 2.5 | 0.18 |
| Open Comedones | 5.4 | 1.8 | −3.6 | −90% | 4.4 | 0.14 |
| Closed Comedones | 5.0 | 4.8 | −0.2 | −3% | 1.8 | 0.81 |
| Cysts | 1.2 | 0.6 | −0.6 | −70% | 0.9 | 0.21 |
| Lesion Erythema | 1.8 | 0.9 | −0.9 | −55% | 0.6 | 0.02** |
| Lesion Elevation | 1.6 | 0.8 | −0.8 | −50% | 0.6 | 0.03** |
| Dryness | 0.2 | 0.0 | −0.2 | −100% | 0.5 | 0.37 |
| Oiliness | 0.2 | 0.2 | 0.0 | 0% | 0.0 | — |

Although the sample size for these preliminary results was small (n=5), statistically significant decreases were seen in the number of papules, the degree of lesion erythema, and the degree of lesion elevation from baseline to 12 weeks. Large numerical differences were seen in three other measurements, differences that were not statistically significant for this small sample size, but that may well become statistically significant as additional data become available: number of pustules, number of open comedones, and number of cysts. With the same caveat about sample size, these preliminary results suggest minimal or no differences resulting from this particular treatment in the number of closed comedones, incidence of dryness, and incidence of oiliness. No adverse events, toxicity, or side effects were reported.

EXAMPLE 10

Dosage and Toxicity

An important consideration is the choice of proper dosage. Proper dosages will be established through otherwise standard dose-response studies and toxicity studies. Because the target area for this treatment is similar to that for hyperhidrosis, similar dosages have been chosen for initial studies. See, e.g., M. Naumann et al., "Focal Hyperhidrosis: Effective Treatment with Intracutaneous Botulism Toxin," *Arch. Dermatol*., vol. 134, pp. 3014 (1998); and M. Naumann et al., "Treatment of Gustatory Sweating with Botulism Toxin," *Ann. Neurol*. vol. 42, pp. 973-975 (1997). There appear to have been no studies defining an accurate dose-response curve for hyperhidrosis, although general clinical guidelines have been generated. See Table 2. Clinical preparations of *botulinum* toxin A, which is made under strict FDA supervision in the United States, are measured in mouse units. A mouse unit, 1 U, is defined as the amount of *botulinum* toxin A that kills fifty percent ($LD_{50}$) of a group of 18-20 gram female Swiss-Weber mice by parenteral injection. Contraindications to the use of *botulinum* toxin A are very few. (Note: There have been reported suggestions that the Botox® unit is 3-5 times as potent as the Dysport® unit. The *botulinum* toxin A used in the experiments reported here was obtained as Botox®; so, to the extent that there may be a difference in the potency of these two commercially available preparations of *botulinum* toxin A, the "units" used in the present specification and claims may be interpreted with reference to Botox® units.)

TABLE 2

| Human Botulinum-A Toxin Predicted Dose-Response |
|---|
| Dosage Unit (U) |
| 1 U = $LD_{50}$ mice ≈ 0.04 ng |
| Clinical Efficacy |
| 1–12 U per kg body weight, depending on patient's response, routine maximum 400 U, delivered not more often than once per 90 days; lower or higher doses may be appropriate for some patients |
| Toxicity |
| Oral: 3,000–250,000 U (monkey)<br>Parenteral: 39 U/kg (monkey)<br>Assumption:<br>Monkey $LD_{50}$ = Human $LD_{50}$<br>Adult $LD_{50}$ = 3000 U |
| Safety Factor |
| toxicity = 40 U/kg |

Based on the preliminary studies reported above, it is expected that in most cases intracutaneous injections should be spaced about 0.5 or 1 cm to about 10 cm apart from one another, preferably about 1.5 to about 3 cm apart; and that the dose per injection site should be about 1 U to about 10 U or 20 U *botulinum* toxin A, preferably about 2 to about 3 U. These dosages may be varied based on individual responses to the injections.

The *botulinum* toxin may be injected intracutaneously or subcutaneously. Alternatively, *botulinum* toxin may be injected intramuscularly at similar doses, particularly when it is desired to simultaneously weaken certain facial muscles, e.g., to reduce rhytids.

Alternatively, the *botulinum* toxin may be applied to the skin as a topical or percutaneous cream, gel, ointment, lotion, aerosol or spray, powder, paste, fixed dressing or other topical or percutaneous administration to provide similar clinical efficacy. Superficial application of the *botulinum* toxin may particularly help to improve comedonal acne, the inflammatory aspects of acne, and topical application may help increase absorption. Such topical administrations are best reconstituted as needed and then stored under refrigeration, as they have a limited shelf life. The shelf life can be extended to a few weeks or longer by adjusting the pH to be slightly acidic, e.g., about pH 5.6. Topical vehicles may include other components used in the art in topical medications, such as vanishing vehicles, moisturizers, emollients, chemical carriers (e.g., DMSO), and buffers known in the art. Typical concentrations of active ingredient may be on the order of 5 to 200 U per mL, depending on the absorption rate and the toxin serotype. In general, the concentration should be adjusted so that the effective rate of administration is equivalent to that of effective injections of *botulinum* toxin. The use of ultrasound, or of an electrophysiological current device, such as iontophoresis, may enhance absorption of topically applied toxin. It is known in the art (albeit using other compounds for treating other conditions) that topically applied agents can reach and clinically affect the sweat glands and sebaceous glands. See, e.g., F. Marzulli et al. (Eds.), "Dermatotoxicology and Pharmacology" in *Advances in Modern Toxicology*, vol 4, John Wiley and Sons, New York (1977).

In preparations that are currently available commercially, *botulinum* toxin A is stored frozen; while *botulinum* toxin B is stored at room temperature.

EXAMPLES 11 AND 12

Preliminary trials have been conducted on topical applications of *botulinum* A toxin with two acne patients. Additional, larger-scale trials of topical applications will be conducted to confirm what types of acne respond well to topical treatment. For the topical treatment, *botulinum* toxin A was reconstituted at a concentration of 100 Units per 0.5 mL of solvent. For the mid-back treatments, the solvent was a 1.4% aqueous solution of polyvinyl alcohol as a neutral ophthalmic solution, and for the left back treatments the solvent was preservative-free saline. A 0.2 mL or 40 U portion of the solution was applied to an area 6 cm×4 cm, patched with Tegaderm™ for 4 hours to avoid disturbances. Results are presented below.

TABLE 3

|  | Patient 1 Baseline | Patient 1 Week 2 | Patient 1 Week 4 | Patient 2 Baseline | Patient 2 Week 2 | Patient 2 Week 4 |
|---|---|---|---|---|---|---|
| Lesions, Mid-Back |  |  |  |  |  |  |
| Papules | 5 | 1 | 0 | 1 | 10 | 2 |
| Pustules | 0 | 0 | 0 | 0 | 0 | 0 |
| Open Comedones | 4 | 1 | 1 | 0 | 0 | 0 |
| Closed Comedones | 0 | 2 | 1 | 11 | 0 | 4 |
| Nodules | 0 | 0 | 0 | 0 | 0 | 0 |
| Lesions, Left Back |  |  |  |  |  |  |
| Papules | 5 | 3 | 3 | 10 | 5 | 3 |
| Pustules | 2 | 0 | 0 | 0 | 0 | 0 |
| Open Comedones | 0 | 0 | 0 | 0 | 0 | 0 |
| Closed Comedones | 0 | 6 | 2 | 4 | 1 | 2 |
| Nodules | 0 | 0 | 0 | 0 | 0 | 0 |

There is a potential emerging trend in these data towards the improvement of acne following the topical application of *botulinum* toxin. Further studies are ongoing. Due to the small number of patients in these initial experiments on topical application, a statistical analysis at this time would have little meaning. Topical application of the *botulinum* toxin to treat acne may eventually prove to be the preferred method of application, both because of the ease of application, and because of the ease of directly delivering the medication directly to affected areas where there is inflammation or other disruption of the skin's tight junctions.

EXAMPLE 13

Further Phase II Clinical Trials will be conducted to confirm that intracutaneous or topical *botulinum* toxin A injections can safely and effectively prevent or decrease the incidence of recalcitrant acne in adults and adolescents. Following Phase II trials, Phase III trials will be conducted, all in accordance with applicable laws and regulations.

The inventors speculate that it is possible that a subpopulation of patients who have previously been treated with *botulinum* toxin for other reasons (e.g., rhytids) may have also incidentally experienced improvements in acne as a side effect. However, to the inventors' knowledge, no previous report has ever suggested the presence of such a side effect of *botulinum* toxin treatment, nor has any previous report suggested that there should be any causal relation between administration of *botulinum* toxin and improvement in acne.

As used in the specification and claims, an "effective amount" of *botulinum* toxin is an amount sufficient to prevent acne, or to inhibit the formation of acne, or to reduce the level of acne, to a clinically significant degree. "Significance" for this purpose is determined as the $P<0.05$ level, or by such other measure of statistical significance as is commonly used in the art for a particular type of experimental determination.

While the preliminary experiments reported above used *botulinum* toxin A, without wishing to be bound by this theory, it is believed that the other *botulinum* toxin serotypes, namely *botulinum* toxins B, C, D, E, F, and G, may also be used in the method of this invention to treat or prevent acne. Proper doses and toxicity will be determined as generally described above for *botulinum* toxin A. There have been suggestions that *botulinum* toxin C may have two variants, one with neurotoxic activity and one lacking such activity. To the extent that such variants of any of the *botulinum* toxin serotypes do exist, the use of all such variants displaying anti-acne activity is considered to be within the scope of this invention.

For example, changing the serotype used might be indicated if a patient develops an immune response to a particular serotype. The dosages and durations of effect may differ among the different serotypes, as will be determined by experiments generally along the lines of those discussed above for serotype A. To reduce the likelihood of developing an immune response, the smallest effective dose for each patient should be used, and the time between successive treatments should made be as long as possible without having substantial symptoms return.

The complete disclosures of all references cited in this specification are hereby incorporated by reference. In the event of an otherwise irreconcilable conflict, however, the present specification shall control.

What is claimed:

1. A method for inhibiting acne vulgans in a human who has acne vulgaris, said method comprising delivering a therapeutically effective amount of *botulinum* toxin A to one or more sites of the skin of the human that have acne vulgaris.

2. A method as recited in claim 1, wherein said delivering comprises the intracutaneous injection of *botulinum* toxin A at multiple sites in the skin, wherein the sites of the injections are separated by about 0.5 to 10 cm.

3. A method as recited in claim 1, wherein said delivering comprises the intracutaneous injection of *botulinum* toxin A at multiple sites in the skin, wherein the sites of the injections are separated by about 1.5 to 3 cm.

4. A method as recited in claim 1, wherein said delivering comprises the topical application of a composition comprising *botulinum* toxin A to one or more sites of the skin that have acne vulgaris.

5. A method as recited in claim 1, wherein said delivering comprises the subcutaneous injection of the *botulinum* toxin A.

6. A method as recited in claim 1, wherein said method is repeated periodically to inhibit the recurrence of acne vulgaris.

7. A method as recited in claim 1, wherein said method is repeated at intervals from about 3 months to about 6 months to inhibit the recurrence of acne vulgaris.

8. A method as recited in claim 1, wherein said method is repeated at intervals of about 4 months to inhibit the recurrence of acne vulgaris.

9. A method as recited in claim 1, wherein said delivering comprises the intracutaneous injection of *botulinum* toxin A at multiple sites in the skin, and wherein between about 1 U and about 20 U of *botulinum* toxin A is injected at each site.

10. A method as recited in claim 1, wherein said delivering comprises the intracutaneous injection of *botulinum* toxin A at multiple sites in the skin, and wherein between about 2 U and about 3 U of *botulinum* toxin A is injected at each site.

11. A method as recited in claim 1, additionally comprising the step of inhibiting at least one rhytid by said delivering of a therapeutically effective amount of *botulinum* toxin A to one or more sites of the skin that have acne vulgaris and that also contain at least one rhytid.

12. A method for inhibiting acne vulgaris in a human who has acne vulgaris, said method comprising the intra-muscular injection of *botulinum* toxin A near one or more sites of the skin of the human that have acne vulgaris.

13. A method for inhibiting acne vulgaris in a human who has acne vulgaris, said method comprising delivering a therapeutically effective amount of *botulinum* toxin to one or more sites of the skin of the human that have acne vulgaris.

14. A method as recited in claim 13, wherein said delivering comprises the intracutaneous injection of *botulinum* toxin at multiple sites in the skin, wherein the sites of the injections are separated by about 0.5 to 10 cm.

15. A method as recited in claim 13, wherein said delivering comprises the intracutaneous injection of *botulinum* toxin at multiple sites in the skin, wherein the sites of the injections are separated by about 1.5 to 3 cm.

16. A method as recited in claim 13, wherein said delivering comprises the topical application of a composition comprising *botulinum* toxin to one or more sites of the skin that have acne vulgaris.

17. A method as recited in claim 13, wherein said delivering comprises the subcutaneous injection of the *botulinum* toxin.

18. A method for inhibiting acne vulgaris in a human who has acne vulgaris, said method comprising the intra-muscular injection of *botulinum* toxin near one or more sites of the skin of the human that to have acne vulgaris.

19. A method as recited in claim 13, wherein said method is repeated periodically to inhibit the recurrence of acne vulgaris.

20. A method as recited in claim 13, wherein said method is repeated at intervals from about 3 months to about 6 months to inhibit the recurrence of acne vulgaris.

21. A method as recited in claim 13, wherein said method is repeated at intervals of about 4 months to inhibit the recurrence of acne vulgaris.

22. A method as recited in claim 13, additionally comprising the step of inhibiting at least one rhytid by said delivering of a therapeutically effective amount of *botulinum* toxin to one or more sites of the skin that have acne vulgaris and that also contain at least one rhytid.

23. A method as recited in claim 13, wherein the *botulinum* toxin comprises *botulinum* toxin B.

24. A method as recited in claim 13, wherein the *botulinum* toxin comprises *botulinum* toxin C.

25. A method as recited in claim 13, wherein the *botulinum* toxin comprises *botulinum* toxin D.

26. A method as recited in claim 13, wherein the *botulinum* toxin comprises *botulinum* toxin E.

27. A method as recited in claim 13, wherein the *botulinum* toxin comprises *botulinum* toxin F.

28. A method as recited in claim 13, wherein the *botulinum* toxin, comprises *botulinum* toxin G.

29. A method as recited in claim 13, additionally comprising the step of inhibiting at least one rhytid by said delivering of a therapeutically, effective amount of a *botulinum* toxin to one or more sites of the skin that have acne vulgaris and that also contain at least one rhytid, wherein the *botulinum* toxin is selected from the group consisting of *botulinum* toxin B, *botulinum* toxin C, botulinurn toxin D, *botulinum* toxin E, *botulinum* toxin F, and *botulinum* toxin G.

* * * * *